United States Patent [19]
Mortimer et al.

[11] Patent Number: 6,140,108
[45] Date of Patent: Oct. 31, 2000

[54] WINE YEAST CULTURES

[75] Inventors: Robert K. Mortimer, Berkeley, Calif.; Bernard Prior, Bloemfontein, South Africa; Clelia Baccari, Berkeley, Calif.

[73] Assignee: The Regents of the University of California, Oakland, Calif.

[21] Appl. No.: 09/008,554

[22] Filed: Jan. 16, 1998

Related U.S. Application Data

[60] Provisional application No. 60/035,539, Jan. 16, 1997.
[51] Int. Cl.[7] .................... C12N 1/00; C12N 1/16; C12N 1/20
[52] U.S. Cl. .................... 435/255.21; 435/253.6; 435/255.1; 435/256.8; 435/911
[58] Field of Search .................... 435/255.7, 255.21, 435/822, 404, 420, 253.6, 255.1, 256.8, 911

[56] References Cited

PUBLICATIONS

Farris et al. A genetically improved wine yeast. Biotechnology Letters. Mar. 1992, vol. 14, No. 3, pp. 219–222.

Romano et al. Improvement of a Wine Saccharomyces cerevisiae Strain by a breeding Program. Applied and Environmental Microbiology. Oct. 1985, vol. 50, No. 4, pp. 1064–1067.

*Primary Examiner*—Leon B. Lankford, Jr.
*Assistant Examiner*—Deborah K. Ware
*Attorney, Agent, or Firm*—Richard Aron Osman

[57] ABSTRACT

The invention provides method and compositions for yeast cultures with a predetermined desirably improved trait, such an enhanced or reduced ability to produce particular fermentation products. In one embodiment, the breeding scheme involves assembling and surveying a large population of natural wine yeast for a chosen trait; select appropriate individuals from this population and repeatedly back-crossing to well-established commercial strain by selecting HO/HO spores from the selected and commercial parental strains, treating asci with zymolase and carrying out spore-spore pairings, observing the spore pairs at intervals to detect formation of primary zygotes, and selecting and sporulating primary zygote clones; analyzing segregants of primary zygote clones and scoring for the trait; selecting the best segregants; and repeating the back-crossing procedure using a different HO/HO spore clone from the commercial parent in each cross.

8 Claims, 2 Drawing Sheets

WINE YEAST CULTURES

This is a continuing application under 35USC120 of U.S. Ser. No. 60/035,539 filed Jan. 16, 1997, abandoned, the specification of which is incorporated herein by reference.

INTRODUCTION

1. Field of the Invention

The invention relates to improved wine yeast cultures.

2. Background of the Invention

While ethanol is the main fermentation product in wine making, a wide variety of other by-products are also produced. Some of these by-products beneficially contribute to the rich chemical diversity of the wine. For example, glycerol can provide a characteristically pleasant "mouthfeel" to the wine. Other fermentation by-products, such as sulfides and ethyl carbamates, are known to detract from wine quality. As the nature of the starter yeast culture largely influences the fermentation products produced, approximately 90% of California wineries choose to inoculate their fermentations with a commercial yeast. These yeast frequently derive from winemakers who have isolated them from apparently successful fermentations. However, there are few opportunities for vintners to more precisely control their fermentations and resultant by-products by starter culture selection. The present invention provides both novel methods for the development of starter wine yeast cultures with more desirable fermentation products and novel cultures produced by the disclosed methods.

Relevant Literature

Mortimer and Hawthorne (1969) Yeast genetics, pp. 385–460, p. 394. In A H Rose and J S Harrison (eds) The yeasts, Vol 1. Biology of yeasts. Academic Press, London; Mortimer et al. (1994) Yeast 10, 1533–1552; Mortimer (1994) American Vineyard 8, 12–19; Romano et al. (1995) J. Appl. Bacteriol. 78, 169–174; Mortimer et al. (1996) in *Oenologie* 95, p. 284–286, A. Lonvaud-Funel, ed. Lavoisier TEC DOC, London, New York, 1996. Zambonelli et al. (1994) Ann.di Microbiol. Ed Enzymol. 44, 107–118.

SUMMARY OF THE INVENTION

The invention provides methods and compositions for yeast cultures with a predetermined desirably improved trait, such an enhanced or reduced ability to produce particular fermentation products, temperature stability (particularly freeze damage resistance), etc. The general methods involve the discovery that genetic differences in strains can provide a significant basis for the natural diversity seen in fermentation products. Coupled with this discovery was the idea of repeatedly back-crossing trait-selected strains with well-established commercial strains to preserve important and often undefined enological properties. In one embodiment, the breeding scheme proceeds as follows (see also, FIGS. 1, 2):

1. Assemble and survey a large population of natural wine yeast for a chosen trait.
2. Select appropriate individuals from this population.
3. Cross to well-established commercial strain.
   3.1 Select HO/HO spores from the selected and commercial parental strains.
   3.2 Treat asci with zymolase and carry out spore-spore pairings. Observe the spore pairs at one to two hour intervals to detect formation of primary zygotes.
   3.3 Select and sporulate primary zygote clones.
4. Analyze segregants of primary zygote clones and score for trait. Select the best segregants.
5. Repeat crossing procedures 3 times using a different HO/HO spore clone from the commercial parent in each cross.

Using HO/HO strains, which are completely homozygous and so any spore pair is the same as any other spore pair, makes planning and crosses much more convenient. Otherwise it is necessary to isolate several primary zygotes and analyze each separately because they all would be potentially different. With heterothallic strains as parents, all zygotes are the same, though heterothallic wine strains are rare. It is also possible to cross the parents to heterothallic strains and isolate a new set of parental strains that are heterothallic. Once the final strain is isolated, they are crossed back to homothallic strains because of the advantages of such strains in wine fermentations.

DESCRIPTION OF THE SPECIFIC EMBODIMENTS OF THE INVENTION

Figure 1:
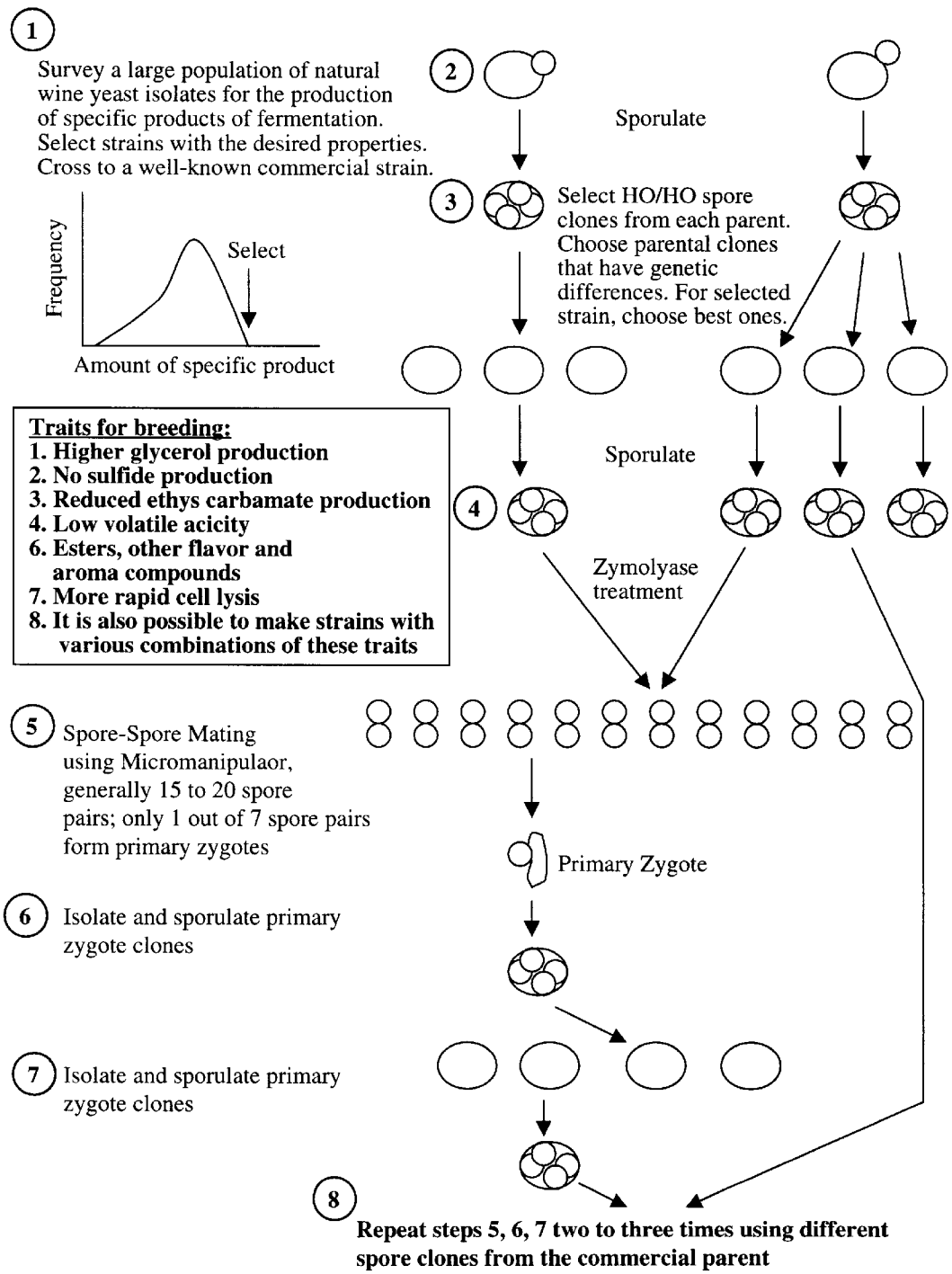
FIG. 1 shows a subject breeding scheme for the development of improved starter yeast cultures.
Figure 2:
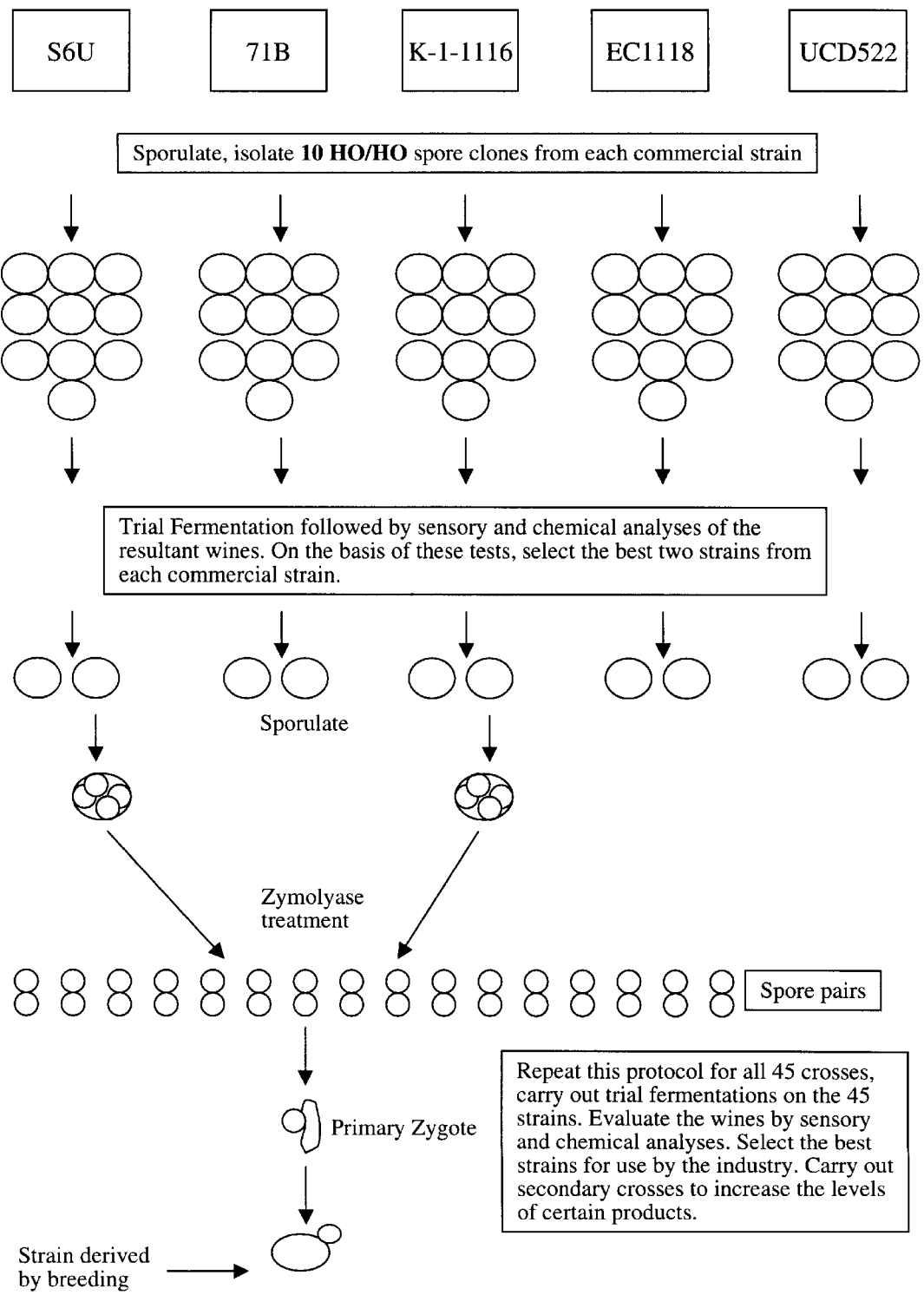
FIG. 2 shows a subject breeding scheme for the development of improved starter yeast cultures including sensory and chemical analysis steps.

General methodologies for breeding of wine yeasts are shown in FIGS. 1 and 2. These methods are generic and can be applied to any trait that can be introduced by breeding, i.e. is present as natural, selectable variants. For examples, the method can be used to develop strains that have the following properties: enhanced amount of glycerol (e.g. at least 10, 15, 18, or 20 g/l glycerol), reduced levels of ethyl carbamate or sulfide production, freeze-damage resistance (e.g. advantageous in frozen yeast products such as doughs), increased lytic propensity (advantageous in sparkling wine production) reduced foaming and reduced levels of volatile acidity, etc. The method can also be used to breed for optimum levels of various flavor and aroma compounds such as esters, by screening a large population of wine yeast by gas chromatography for products formed during fermentations of wine musts. In addition, it should be possible to construct strains that lyse more readily.

The general methodologies were implemented as follows. The first step was to screen a large collection of strains that had been isolated from natural fermentations for the production of particular products formed during fermentation and to select the appropriate strain from among these strains. A well-established commercial strain was also chosen as the other parent in the breeding schedule, with one of the goals being to introduce new traits into this established commercial strain.

One of the selected strains and the commercial strain were sporulated and individual spores were isolated by micromanipulation. The resultant spore clones from each parent were then tested for various traits such as fermentatio of various sugars and resistance to copper. The spore clones were also tested for their abilities to sporulate and for the production of sulfides. Spore clones will sporulate because of the homothallism gene; such clones originate from a haploid spore that had diploidized due to homothallic switching of the mating type locus (Herskowitz et al. 1992) and are completely homozygous. Parental clones were selectd from these clones and this selection was based on the ability to sporulate, to produce no sulfides and to have at least one additional genetic difference between the two parental clones.

Asci from the two parental clones were than treated with zymolyase to remove the ascus walls and to free the ascospores. With a micromanipulator, spores were then paired up, one spore from each parent in each pair, along a line scratched on the surface of the microdissections agar. Fifteen to twenty such pairs were arranged along the line and these pairs were then observed every hour to two hours for up to 6 hours. The goal was to detect those spore pairs that had mated to form primary zygotes. Periodic examination is necessary because only about 1 in 7 spore pairs forms a primary zygote but zygotes are present in most of the other clones due to homothallic switching at the mating type locus in one or both of the parental cells. The sporulated and spore tetrads were isolated by micromanipulation from the asci (see, Winge and Lausten 1938, Romano et al. 1995).

The spore clones from this primary zygote clone were then tested for the various traits that might be segregating. If the chosen genetic difference (e.g. Maltose fermentation) between the parental clones is segregating, then the primary zygote is considered to have arisen from a true mating. If not then the zygote was only apparent and another zygote must be used. Such apparent zygotes happen not infrequently. The spores from the true primary zygotes were then tested for sulfide production and those clones that produced no sulfide were selected.

These selected clones were then sporulated and asci were dissected. The resultant spores then served as parental cells for the second cross. The other parent was another homothallic (HO/HO) spore clone from the commercial parent. The above spore-spore pairings and isolation of primary zygote clones were then repeated and the whole process was then repeated an additional two to three times.

EXAMPLES

Yeast Strains: Cultures of *Saccharomyces cerevisiae* evaluated for their ability to produce glycerol were obtained from the Genetic Stock Collection (Berkeley, Calif.) and included three haploid laboratory strains, six commercial strains and 27 and 159 strains obtained respectively from spontaneous wine fermentations isolated in Italy (Mortimer et al., 1994, supra.) and California. The breeding stock for the hybridization program consisted of natural yeast strain Ba25 (Mortimer et al. 1994) and a commercial strain (Premier Cuvee [PC], Universal Foods Corporation; Milwaukee, Wis.).

Media and cultivation: The strains were inoculated in 1 ml YPD broth (1% glucose, 2% peptone, 1% yeast extract) and grown overnight at 30° C. with vigorous agitation. The culture (0.5 ml) was transferred into 5 ml of a synthetic wine (YEP) medium (0.2% yeast extract, 2% peptone, 0.1% $Kh_2PO_4$, 20% glucose, pH 3.2; Radler and Schültz, 1982). The cultures were incubated at 23° C. for seven days, centrifuged and the supernatants were held for analysis. A more detailed analysis of the fermentation in 450 ml YEP medium was conducted at 23° C. in 500 ml Erlenmeyer flasks equipped with side-arm cuvettes and stirred with magnetic stirring bars.

Genetic Techniques: Spore-spore matings and zygote and haploid spore isolations were carried out by micromanipulation as described by Mortimer and Hawthorne (1969).

Analysis: Glycerol levels were determined by using a glycerol test kit (Boehringer Mannheim Cat. No 148 270). Ethanol levels were determined either using a test kit (Boehringer Mannheim Cat. No 176 290) or quantified by gas chromatography using a Hewlett Packard Model 5710A gas chromatograph. Acetic acid and acetaldehyde were determined by gas chromatography (Stanley and Pamment, 1995).

Results: The mean glycerol levels produced by 187 strain of *S. cerevisiae* cultivated in 200 g/l YEP broth for seven days was 4.2 g/l (FIG. 1) and ranged between 1.5 g/l and 5.6 g/l. The mean glycerol concentrations produced by three laboratory strains was 2.0 g/l (range 1.5–2.5 g/l) which is considerably lower than that observed for the six commercial wine strains (mean of 3.9 g/l; range between 3.3 and 4.5 g/l), the 27 strains isolated from the natural wine fermentations in Italy (mean of 3.7 g/l; range between 3.1 and 5.1 g/l) and 151 strains isolated from natural wine fermentations in California (mean of 4.5 g/l; range between 2.8 and 5.6 g/l). These values are in a similar range to those observed in various wines (Mattick and Rice, 1970; Ough et al., 1972; Rankine and Bridson, 1971). A selection of the strains was examined in greater detail for their ability to produce glycerol and ethanol in Zinfandel grape must (Table 1). The laboratory strain W 303-1A fermented both glucose YEP and must poorly. The commercial and natural fermentation strains, on the other hand, produced both higher glycerol and ethanol concentrations in must than in the synthetic grape must (YEP) but the ratio of ethanol to glycerol was lower in must than in YEP indicating that the medium can affect the balance between glycerol and ethanol. Numerous factors including temperature, pH, nitrogen source have been found to influence the ratio of ethanol to glycerol produced by yeast (Proir and Hohmann, 1997).

Commercial wine yeasts Prise de Mousse and Premier Cuveé with two strains isolated from natural wine fermentations (Ba 25 and Bb 25 [8]) were selected for a breeding program. The cultures were sporulated and at least five asci of each strain were dissected. The spores were evaluated for their ability to produce ethanol and glycerol in glucose (20%)-YEP medium, for their segregation patterns on sucrose, maltose, galactose, copper, minimal, $H_2S$ (Biggy) media and for their ability to sporulate. The concentrations of glycerol and ethanol produced by the segregants were either higher or lower than those of the parent strains indicating possible genetic segregation of the ability to produce these fermentation products (Table 2). All cultures fermented sucrose and maltose and none of the spores was petite. Most of the natural wine strains but not the commercial isolates fermented galactose. No clear segregation pattern was observed for the ability of the spores to sporulate, grow in the presence of copper or to produce $H_2S$.

A Premier Cuveé spore (spore 25A) that was able to sporulate and gave the lowest ratio of ethanol to glycerol (8.2) was selected for mating with a Ba25 spore (3C) that also sporulated and was found to produce a high glycerol level (8.2 g/l) and had a low ethanol/glycerol ratio (6.9). The zygotes were sporulated and the glycerol and ethanol levels and other phenotypic characteristics of the spores were evaluated. A spore with a low ethanol/glycerol ratio and high glycerol level was selected to back-cross to the original spore 25A of the Premier Cuveé strain. This back-crossing, sporulation and phenotypic evaluation was repeated three times and the results are presented in Table 3.

High glycerol strains developed by this method on deposit with the Yeast Genetics Stock Center, University of California, Berkeley, Berkeley, Calif., include:

1. XPB3-1C
2. XPB3-1D
3. XPB3-2B
4. XPB3-2C
5. XPB3-3A
5. XPB3-3D
6. XPB3-4C
7. XPB3-4D
8. XPB3-5B
9. XPB3-5C
10. XMB2
11. XMB3
12. XMB4
13. XMB5
14. XMB6

Development of Strains that Produce no sulfides: Sulfide, formed from sulfate, is used in the biosynthesis of methionine and cysteine. The final step before sulfide is controlled by the sulfide reductase enzymatic genes, some of which are responsible for the synthesis of the proteins in this complex. During a genetic examination of 28 strains of *Saccharomyces cerevisiae* that had been isolated from fermentations in the Italian Region of Emilia Romagna we found two strains, Ba25 and Ba220, that were heterozygous for met5, one of the genes controlling the synthesis of the sulfite reductase complex (Mortimer et al 1994). Strains bearing this mutation make no sulfides but would be expected to produce elevated levels of sulfite. We crossed this mutation, derived from dissection of asci from Ba25, into a Prisse de Mousse genetic background through repeated backcrosses to this commercial strain. This strain development was straightforward because the trait is under the control of a single gene that is easily scored.

Zero sulfide strains developed by this method on deposit with the Yeast Genetics Stock Center, University of California, Berkeley, Berkeley, Calif., include: XMB1(1)-1D, XMB1(1)-2C, XMB1(1)-3C, XMB1(2)-2A and XMB1(2)-4B It is important to emphasize that in our approach to breeding of wine yeast, no molecular procedures have been used. The breeding is based only on existing genetic diversity already present in the natural wine strains. Other groups have incorporated cloned genes into wine yeast to achieve malo-lactic fermentations or to increase glycerol production, but such strains can not be used because of existing public disapproval and also because of regulatory problems.

Production of sulfides during fermentations is considered to be the second most significant problem facing winemakers according to a recent survey carried out by the American Vineyard Foundation. With one of the strains which we have developed used as an inoculum, no sulfides will be produced by this strain. Of course, native yeast that also get into the fermentation will produce sulfides, however this will not be a major problem because we have found that Prise de Mousse has a high persistence level in inoculated fermentations (Table 1). That is, at the end of fermentation, fairly high percentages of the *Saccharomyces cerevisiae* cells present are from the inoculum.

TABLE 1

Glycerol and ethanol production (mean of three determinations with the standard deviation in parentheses) by selected *S. cerevisiae* strains cultivated in Zinfandal grape must and defined medium (YEP containing 29% glucose)

| Strain | Glycerol (g/l) | | Ethanol (g/l) | | Ethanol/Glycerol ratio | |
| --- | --- | --- | --- | --- | --- | --- |
| | YEP | Must | YEP | Must | YEP | Must |
| Laboratory Strain | | | | | | |
| W 303-1A | 4.0 (0.6) | 3.3 (0.8) | 39.6 (3.2) | 21.2 (1.4) | 5.3 | 6.4 |
| Commercial wine yeasts | | | | | | |
| French Red | 4.0 (1.2) | 8.5 (0.8) | 58.2 (4.3) | 94.0 (5.3) | 15.8 | 11.1 |
| Montachet | 3.3 (1.2) | 8.3 (1.1) | 50.2 (6.8) | 64.1 (8.8) | 14.4 | 7.7 |
| Prise de Mousse | 3.9 (1.5) | 8.7 (0.6) | 56.2 (3.1) | 63.5 (6.2) | 14.4 | 7.3 |
| Premier Cuveé | 4.5 (0.1) | 7.7 (0.3) | 60.8 (2.6) | 72.0 (11.1) | 13.5 | 9.4 |
| Lallemand K1 | 3.6 (0.2) | 7.9 (0.1) | 53.8 (3.0) | 82.4 (8.9) | 14.9 | 10.4 |
| Bordeaux | 4.2 (0.1) | 6.6 (0.2) | 60.7 (3.9) | 74.2 (7.2) | 14.5 | 11.2 |
| Mean wine yeasts | 3.9 | 8.0 | 56.6 | 75.0 | 14.5 | 9.4 |
| Natural wine yeasts | | | | | | |
| Ba 25 | 4.9 (1.6) | 10.9 (0.9) | 65.2 (6.1) | 82.6 (7.7) | 13.3 | 7.6 |
| Ba 126 | 3.6 (0.8) | 10.3 (0.6) | 27.4 (2.5) | 83.2 (12.2) | 7.6 | 8.1 |
| Ba 137 | 4.2 (0.9) | 7.1 (0.5) | 41.2 (0.6) | 57.3 (2.9) | 9.8 | 8.1 |
| Ba 220 | 3.0 (0.8) | 7.2 (0.8) | 62.4 (6.7) | 79.8 (11.5) | 20.8 | 11.1 |
| Bb 23 (1) | 5.1 (0.4) | 9.9 (1.3) | 42.8 (2.1) | 83.5 (7.1) | 18.4 | 8.4 |
| Bb 25 (8) | 5.5 (0.6) | 7.5 (0.7) | 59.2 (2.6) | 75.7 (9.9) | 10.8 | 10.1 |
| Ba 30 (5) | 5.1 (0.3) | 9.7 (0.2) | 68.4 (3.7) | 93.9 (6.9) | 13.4 | 9.6 |
| Bb 32 (5) | 4.6 (0.9) | 8.9 (0.9) | 63.6 (0.7) | 85.2 (8.2) | 13.8 | 9.5 |
| Bb 19 (4) | 4.9 (0.2) | 7.7 (1.3) | 54.6 (2.2) | 60.7 (4.2) | 11.1 | 7.9 |
| Bb 22 (4) | 5.6 (0.7) | 8.1 (0.2) | 58.1 (1.8) | 90.9 (6.6) | 10.4 | 11.2 |
| Mean natural yeasts | 4.7 | 8.7 | 54.3 | 79.3 | 11.6 | 9.1 |

TABLE 2

Production of glycerol and ethanol (mean of at least three
determinations) by wine yeasts and their segregants.

| Wine yeast strains | Glycerol (g/l) Parent | Glycerol (g/l) Segregants[1] | Ethanol (g/l) Parent | Ethanol (g/l) Segregants[1] | Ethanol/glycerol ratio Parent | Ethanol/glycerol ratio Segregants[1] |
|---|---|---|---|---|---|---|
| Commercial |  |  |  |  |  |  |
| Prise de Mousse | 3.9 | 2.7–6.7 | 56.2 | 40.4–71.2 | 14.4 | 7.3–22.4 |
| Premier Cuveé | 4.5 | 4.1–7.0 | 60.8 | 42.7–76.3 | 13.5 | 8.2–17.3 |
| Natural |  |  |  |  |  |  |
| Ba 25 | 7.3 | 4.2–8.2 | 51.0 | 26.1–62.4 | 7.0 | 4.6–11.6 |
| Ba 25 (8) | 5.0 | 4.0–7.6 | 66.3 | 56.0–72.0 | 13.3 | 9.5–15.7 |

[1]Range of concentrations

TABLE 3

Means of glycerol and ethanol concentrations produced by
S. cerevisiae parents and progeny in glucose (20%) - YEP medium

| Strain | Glycerol (g/l) | Ethanol (g/l) | Ratio Ethanol/ glycerol |
|---|---|---|---|
| Parents |  |  |  |
| Premier Cuveé | 4.5 (0.1)[b] | 60.8 (2.6)[b] | 13.5 |
| Premier Cuveé spores (14)[a] | 5.2 (4.1–7.0)[c] | 60.6 (42.7–79.8)[c] | 11.7 |
| Premier Cuveé spores 25A | 5.3 (1.4)[b] | 43.9 (3.6)[b] | 8.2 |
| Ba 25 | 7.3 (2.0)[b] | 51.0 (7.8)[b] | 7.0 |
| Ba 25 spores (16)[a] | 6.7 (4.2–9.3)[c] | 46.7 (26.1–63.6)[c] | 7.0 |
| Ba 25 spore 3C | 8.2 (0.7)[b] | 56.5 (1.7)[b] | 6.9 |
| First backcross (Ba 25-3c × PC-25A) |  |  |  |
| Spores (28)[a] | 9.0 (5.3–14.1)[c] | 81.3 (60.6–92.2)[c] | 9.0 |
| Spore 8B | 13.3 (0.6)[b] | 80.0 (1.6)[b] | 6.0 |
| Second Backcross (PC-25A × spore 8B) |  |  |  |
| Spores (51)[a] | 9.8 (5.2–16.6)[c] | 64.7 (51.5–78.6)[c] | 6.6 |
| Spore 2D | 15.0 (0.2)[b] | 73.6 (1.5)[b] | 4.9 |
| Third Backcross (PC-25A × spore 2D) |  |  |  |
| Spores (20)[a] | 11.5 (4.9–18.1)[c] | 80.2 (71.1–92.9)[c] | 6.9 |

[a]Number of spores tested
[b]Standard deviation of at least three independent determinations
[c]Range of concentrations

TABLE 4

Glycerol and ethanol production (mean of four independent
determinations with standard deviations in parentheses) and galactose
fermentation by S. cerevisiae parents and segregants in
glucose (20%) - YEP medium

| Strain | Glycerol (g/l) | Ethanol (g/l) | Ratio Ethanol/ Glycerol | Galactose utilization |
|---|---|---|---|---|
| Premier Cuveé spore 25A | 5.3 | 43.9 | 8.2 | – |
| Spore 2D from second backcross | 15.0 | 73.6 | 4.9 | 0 |
| Tetrads |  |  |  |  |
| 1A | 8.8 (0.4) L | 78.3 (4.4) L | 8.9 | – |
| 1B | 8.1 (0.4) L | 85.0 (2.2) H | 10.5 | + |
| 1C | 13.7 (0.9) H | 83.9 (1.6) H | 6.1 | – |
| 1D | 13.7 (1.6) H | 76.9 (4.3) L | 5.6 | + |
| 2A | 6.8 (0.4) L | 92.9 (2.0) H | 13.6 | + |
| 2B | 14.1 (0.7) H | 84.3 (1.2) L | 6.0 | – |
| 2C | 16.7 (0.3) H | 76.9 (1.2) L | 4.6 | + |
| 2D | 9.1 (1.2) L | 84.4 (0.6) H | 9.3 | – |
| 3A | 14.1 (1.8) H | 71.1 (4.3) L | 5.0 | – |
| 3B | 6.9 (1.1) L | 86.1 (1.4) H | 12.5 | + |
| 3C | 4.9 (0.4) L | 85.9 (0.8) H | 17.6 | – |
| 3D | 16.7 (2.4) H | 71.4 (4.8) L | 4.3 | + |
| 4A | 7.1 (1.1) L | 87.1 (0.9) H | 12.3 | + |
| 4B | 10.1 (1.0) L | 79.6 (2.7) H | 7.9 | – |
| 4C | 16.9 (1.6) H | 77.2 (1.3) L | 4.6 | – |
| 4D | 15.7 (0.4) H | 74.7 (3.0) L | 4.8 | + |
| 5A | 8.3 (0.4) L | 80.1 (3.6) H | 9.7 | – |
| 5B | 18.1 (0.6) H | 76.1 (1.3) L | 4.2 | – |
| 5C | 12.7 (1.0) H | 74.2 (1.4) L | 5.8 | + |
| 5D | 8.5 (0.6) L | 77.9 (1.1) H | 9.1 | + |

What is claimed is:

1. A method for making an improved starter wine yeast culture, which culture comprises an improved trait that can be introduced by breeding, said method comprising steps:

a) assembling and surveying a population of natural wine yeast for an improved trait;

b) selecting from said population yeast cells comprising said improved trait;

c) crossing said cells to a well-established commercial strain by:
      i) selecting HO/HO spores from said cells and said commercial strain;
      ii) treating resultant asci with zymolase and carrying out spore-spore pairings;
      iii) observing the spore pairs at intervals to detect formation of primary zygotes;
      iv) selecting and sporulating primary zygote clones;

d) analyzing segregants of said primary zygote clones and scoring said clones for said trait;

e) selecting segregants presenting most improvement in said trait;

f) repeating crossing step c) using a different HO/HO spore clone from the commercial parent in each cross; wherein a culture comprising said improved trait is obtained.

2. A method according to claim 1, wherein said intervals are about one to two hour intervals and step f) comprises repeating crossing step c) at least three times.

3. A method according to claim 1, wherein said improved trait is the ability to produce an improved amount of a fermentation product.

4. A method according to claim 1, wherein said improved trait is the ability to produce an enhanced amount of glycerol or flavor compounds or a reduced amount of a sulfide, an ethyl carbamate, foaming or a foam promoting compound, or acidity.

5. A method according to claim 1, wherein said improved trait is the ability to produce at least 15 g/l glycerol.

6. A method according to claim 1, wherein said improved trait is freeze-damage resistance.

7. An improved starter wine yeast culture produced according to the method of claim 1, wherein said improved trait is the ability to produce at least 15 g/l glycerol.

8. An improved starter wine yeast culture produced according to the method of claim 2, wherein said improved trait is the ability to produce at least 15 g/l glycerol.

* * * * *